United States Patent
Pickart

(10) Patent No.: US 8,183,204 B2
(45) Date of Patent: May 22, 2012

(54) METHODS AND COMPOSITIONS FOR INCREASING SKIN REMODELING

(75) Inventor: Loren R. Pickart, Bellevue, WA (US)

(73) Assignee: Summit Associates International Inc., Bellevue, WA (US)

(*) Notice: Subject to any disclaimer, the term of this patent is extended or adjusted under 35 U.S.C. 154(b) by 0 days.

(21) Appl. No.: 12/169,548

(22) Filed: Jul. 8, 2008

(65) Prior Publication Data

US 2009/0137458 A1    May 28, 2009

Related U.S. Application Data

(63) Continuation of application No. 09/976,646, filed on Oct. 11, 2001, now abandoned.

(60) Provisional application No. 60/239,831, filed on Oct. 11, 2000.

(51) Int. Cl.
   *A61K 38/02*    (2006.01)

(52) U.S. Cl. .............................. 514/6; 514/1.1

(58) Field of Classification Search .................. None
   See application file for complete search history.

(56) References Cited

U.S. PATENT DOCUMENTS

| 4,283,386 | A |   | 8/1981  | Van Scott |         |
|-----------|---|---|---------|-----------|---------|
| 5,118,665 | A |   | 6/1992  | Pickart   |         |
| 5,120,831 | A |   | 6/1992  | Pickart   |         |
| 5,135,913 | A |   | 8/1992  | Pickart   |         |
| 5,164,367 | A |   | 11/1992 | Pickart   |         |
| 5,348,943 | A |   | 9/1994  | Pickart   |         |
| 5,382,431 | A | * | 1/1995  | Pickart   | 424/401 |
| 5,550,183 | A |   | 8/1996  | Pickart   |         |
| 5,554,375 | A |   | 9/1996  | Pickart   |         |
| 5,698,184 | A |   | 12/1997 | Pickart   |         |
| 5,888,522 | A |   | 3/1999  | Pickart   |         |

* cited by examiner

*Primary Examiner* — Christopher R. Tate
*Assistant Examiner* — Roy Teller
(74) *Attorney, Agent, or Firm* — Christensen O'Connor Johnson Kindness PLLC

(57) ABSTRACT

Skin remodeling is stimulated at the site of blemished skin using an ionic metal-peptide complex to diminish or remove the skin imperfection. The blemish can be a scar, especially surgical or wound scars, acne scars, keloid scars, and the like, or a skin tag, callus, benign skin mole, stretch marks, facial keratosis, thickened sunspots of the skin, or a vitiligo spot. The peptide-ionic metal complex is comprised of an ionic metal selected from copper(II), tin(II), tin(IV), and zinc(II), and salts thereof, and the peptide component can be a hydrolysis of casein, collagen, elastin, meat products, silk protein, or soybean protein, or a chemically synthesized dipeptide, tripeptide, tetrapeptide or the like which complexes with the ionic metal.

13 Claims, No Drawings

```
                              SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:  Synthetic
      peptide molecules

<400> SEQUENCE: 1

Gly His Lys His
  1
```

METHODS AND COMPOSITIONS FOR INCREASING SKIN REMODELING

RELATED APPLICATIONS

This application is a Continuation of U.S. patent application Ser. No. 09/976,646, filed Oct. 11, 2001 which claims priority to U.S. Provisional Patent Application No. 60/239,831, filed Oct. 11, 2000, incorporated herein by reference in its entirety.

BACKGROUND OF THE INVENTION

The treatment of skin imperfections such as scars, solar keratosis (sun damages marks), age spots, vitiligo marks, skin tags, calluses, keloids, moles, pigmentations, and stretch marks remains a major problem despite the development of numerous treatments such as the use of silicone sheets, scar subcision, deep chemical peels, laser resurfacing, dermabrasion and so forth. The problem with current techniques for removal of skin imperfections is that they all are poorly effective, expensive and often painful. And, if the dermatologist or esthetician performing the procedure is not highly skilled, the results can produce further scarring.

An alternative to removing skin imperfections is to enhance a natural biological process termed "skin remodeling." During the process of skin remodeling a wounded area which has healed is slowly reconstructed to remove the residual scars and imperfections. This smoothes the skin and blends the skin with nearby undamaged skin. Scar collagen is removed and replaced with a mixture of skin cells and collagen fibers. This skin remodeling may continue in a skin area for 10 years. In children the remodeling rate is high and scars and other types of imperfections are usually rapidly removed from injured or disfigured skin areas. But as individuals reach adulthood, this rate diminishes and small scars and lesions may remain for many years.

One way to accelerate remodeling is the use of exfoliating chemicals to speed skin shedding; in stronger versions they are used as "chemical peels". Likewise, biochemicals such as retinol and retinoic acid activate systems that increase skin breakdown and resynthesis. Another way to accelerate skin remodeling is with the use of skin regeneration accelerators that enhance the skin's production of collagen and elastin. The use of skin regeneration accelerators can be combined with the methods that cause controlled skin damage.

Van Scott (U.S. Pat. No. 4,283,386) indicates that metallic (copper, zinc, or aluminum) salt forms of cysteic acid, cysteine sulfinic acid and homocysteic acid produce remissions of dry and broken skin, keratoses, warts and palmar and plantar hyperkeratosis.

SUMMARY OF THE INVENTION

The present invention provides, in one aspect, a method for stimulating remodeling of blemished skin in a mammal, including humans. A composition is administered to the skin imperfection or blemish that comprises a ionic metal-peptide complex in an amount effective to remodel the skin and diminish or remove the skin blemish. The skin blemish which is removed can be a scar, such as a surgical scar, a wound scar, an acne scar, a keloid scar, a burn scar, or a scar developed as a result of Sjogren's syndrome. In other aspects the skin blemish can be a skin tag, callus, benign skin mole, stretch marks, facial keratosis, thickened sunspots of the skin, or a vitiligo spot.

According to the invention, the peptide-ionic metal complex is comprised of an ionic metal selected from the group consisting of copper(II), tin(II), tin(IV), and zinc(II), and therapeutically acceptable salts and complexes thereof. The peptide component of the complex can be a hydrolysis of casein, collagen, elastin, meat products, silk protein, or soybean protein, such as hydrolysis formed enzymatically, with acid, base, bacteria, or the like. The peptide can also be prepared by chemical synthesis. Typically, the composition will be administered topically or by injection into the skin, and the concentration of the ionic metal-peptide complex in the composition, although it can vary widely depending on the particular use, is typically about 1% to about 25%.

In yet another aspect the invention provides a method for inhibiting the development of a scar following a surgical incision in the skin. A pharmaceutical composition is administered to the skin at the incision site, which composition comprises a ionic metal-peptide complex in an amount effective to remodel the skin and inhibit development of a scar at the site.

DETAILED DESCRIPTION OF THE SPECIFIC EMBODIMENTS

Treatment methods and compositions are provided to enhance the removal of scars, lesions and imperfections, such as scars of surgical, acne, or burn origin, calluses, benign moles, facial keratosis, vitiligo marks, and the like, using metal ions complexed with peptides to facilitate and speed the process of skin remodeling. The methods comprise administering to the scar or site of skin imperfection a therapeutically effective amount of a composition which comprises the peptide-metal complex described herein in an amount and for a length of time sufficient to enhance the skin remodeling process. For administration to a scar, lesion or blemish, the epidermal layer of skin is intact, as opposed to an open wound or sore, or other condition in which the skin is broken. In another aspect of the invention, the methods and compositions are used to prevent surgical scars, and thus are administered immediately following surgery for the specific purpose of inhibiting development of scar tissue at the incision site.

The methods can be used to reduce surgical scar formation by administering the peptide-metal complexes immediately after surgery. The methods comprise administering to the incision area a prophylactically effective amount of a composition comprising a peptide-metal complex.

As used herein it will be understood that "peptide" refers to synthetically and biologically produced peptides, as well as to peptone mixtures which are obtained by the hydrolysis of larger peptides, polypeptides and proteins.

Peptones are generally comprised of intermediate polypeptide products and mixtures of small peptides, formed in partial hydrolysis of proteins. Among the types of protein digests useful in the invention are digests of soybean protein, casein, collagen, elastin, meat products (e.g., PRIMATONE), such as beef, liver, silk protein and so forth. By peptone digest is meant that the protein is degraded by enzymatic digestion or by acid or base hydrolysis, or by the bacterial cultures that internally hydrolyze proteins and secrete the subsequent peptides, of by bacterial cultures that secrete hydrolytic enzymes in a culture medium which then hydrolyze proteins in the culture medium, according to well known procedures, such as described in Remington's Pharmaceutical Sciences, Mack Publishing Co., Easton, Pa. pp. 428-429 (1975), which is incorporated herein by reference, using enzymes such as papain, etc. Many peptone digests are widely available commercially, such as from Sigma Chemical Company, St. Louis, Mo.

Synthetic peptides include dipeptide and tripeptide molecules such as Gly-His-Lys, Gly-His-Lys-His (SEQ ID NO: 1), Gly-Gly-His, His-Gly-Gly, Gly-Gly, Gly-Gly-Gly, Ala-Gly-His, Phe-Phe, Gly-Cys-Gly, and His-Gly-His, tetrapeptides, pentapeptides, hexapeptides, and the like, as virtually any small peptide which complexes with the ionic metals as described herein will function in the context of the present invention. Synthetic peptides are commercially available from a wide variety of sources, such as Sigma Chemical Company, St. Louis, Mo.

Metal Salts and Metal Complexes

Ionic metal complexes of copper, tin and zinc, or the salts thereof, such as sulfate, acetate, phosphate, gluconate, di-D-gluconate, acetyl tyrosinate, aspartate, methylsilanol, acetylmethionate, bis(N-acetyl-1-methioninato-, PCA (L-proline, 5-oxo-), PCA methylsilanol, USNATE (1,3-(2H, 9bh)-dibenzofurandione, 2,6-diacetyl-7,9-dihydroxy-8,9b-dimethyl-) and other complexing agents. Such metal complexes are widely available commercially, such as from Sigma Chemical Company, St. Louis, Mo.

Formation of Metal Organic Complexes

A peptide is combined with an amount of an aqueous solution of transition metal salt sufficient to form a complex. The process is described in U.S. Pat. Nos. 5,382,431 and 5,888,522, and pending application Ser. No. 09/280,459, the disclosures of each being expressly incorporated herein by reference.

Typically, the complex is then combined with a pharmaceutically acceptable carrier to form a cream, lotion, or solution in a concentration of from about 0.1% to about 25% peptide-metal complex or more. The preparation may be sterilized or pasteurized, as desired, without destroying the skin lesion removal activity of the peptide-metal complex.

To produce the complexes useful in the present invention, the peptides are complexed with one or more ionic transition metals, such as copper, tin, or the salts thereof, such as sulfate, acetate, phosphate, etc., as described above. In one method for preparing the organic-metal complex, the peptide is dissolved in warm water (about 40° C. to 60° C.) at a concentration of about 20 to 50% (weight/volume), then mixed with a aqueous solution of a metal salt complex at a salt concentration of about 10 to 50% (w/v). If desired, isolation and purification of the peptone-copper complexes can then be accomplished by any suitable separation or purification procedure such as, for example, filtration, extraction, centrifugation, crystallization, or a combination of these procedures.

By complexed is meant that the peptides and metal ions form electrostatic bonds, although this mechanism is offered by way of possible explanation only and not by way of limitation.

The pH of the mixture is adjusted (with sodium hydroxide or the like) to a pH between 5.0 and 7.0, and other aqueous components, as desired, are added, followed by blending in of carriers, smootheners, etc. for preparing a final formulation.

The peptide-metal complexes of the invention may be administered for a variety of therapeutic, prophylactic or cosmetic uses as described herein to humans or in veterinary applications to other warm-blooded animals. Among veterinary animals particularly well suited for treatment with the present compositions are species of equine, bovine, porcine, ovine, caprine, canine, avian, feline, etc. Show animals suffering from or susceptible to scarring are particularly well suited for treatment according to the present invention.

The compositions and pharmaceutical preparations thereof are intended for local, topical, oral or parenteral (e.g., subcutaneous injection) administration for prophylactic and/or therapeutic or a cosmetic treatment regimen, to facilitate natural skin remodeling. Preferably, the compositions, including pharmaceutical compositions, are administered are administered locally, e.g., topically, as a paste, cream, ointment, salve, lotion, gel, spray, etc., separately or in conjunction with a wound dressing, bandage, and the like.

For administration to warm-blooded animals, the peptide-metal compositions will typically be sterilized and incorporated in pharmaceutical or veterinary formulations. Such compositions can be sterilized by conventional, well-known sterilization techniques, e.g., boiling or pasteurization, without substantially adversely affecting the biological activity of the peptide-metal complexes. The compositions may contain pharmaceutically acceptable auxiliary substances as may be required to approximate physiological conditions and as may be desirable to prepare compositions for convenient administration, such an pH adjusting and buffering agents, and delivery vehicles.

Actual methods for preparing pharmaceutically administrable compounds will be known or apparent to those skilled in the art and are described in detail in, for example, Remington's Pharmaceutical Science, supra.

Depending on the intended mode of administration and the intended use, the compositions may be in the form of solid, semi-solid, or liquid dosage forms, such as, for example, powders, granules, crystals, liquids, suspensions, liposomes, pastes, creams, salves, etc., and may be in unit-dosage forms suitable for administration of relatively precise dosages. The compositions may include a conventional pharmaceutical carrier or excipient and, in addition, may include other medicinal agents, growth factors, wound sealants, carriers, etc., as further described below.

For semi-solid compositions, as would be appropriate for pastes and creams intended for topical administration, the peptide-metal complexes can be provided separately or may be compounded with conventional nontoxic carriers such as, for example, aloe vera gel, squalene, glycerol stearate, polyethylene glycol, cetyl alcohol, stearic acid, and propylene glycol, among others. Such compositions may contain about 1-50% active ingredient, more preferably about 1-25%. Thus, the final concentration of copper or other metal in a formulation can range from about 0.1 or 0.15% (w/v) up to 0.4 to 0.8% or 1.6%, and in some instances up to 2 to 5% or more, although it will typically be desirable to employ the lowest final concentration of copper or other metal as possible which achieves the desired effect.

The concentration of the peptide-metal complexes in these formulations can vary widely, and will be selected primarily by intended use, viscosities, etc., in accordance with the those skilled in this art; for example, see Remington's Pharmaceutical Science, 17th ed., Mack Publishing Company, Easton, Pa. (1985), which in incorporated herein by reference. The composition or formulation to be administered will, in any event, contain a quantity of the peptide-metal complexes sufficient to achieve the desired skin remodeling effect in the subject being treated.

The compositions of the invention are administered to a warm-blooded animal, such as humans, already suffering from a skin blemish, lesion or other imperfection, or prophylactically after surgical incision to reduce scar formation. Amounts adequate to accomplish these effects are defined as a "therapeutically effective doses." Amounts effective for this use will depend on the severity of the lesion or surgical wound but generally range from about 0.1 mg to about 50 mg per day of peptide-metal complex per day per square centimeter of wound site, with dosages of from about 1 mg to 25 mg, sometimes about 3, 5 or 10 mg up to about 15 or 20 mg per day per square centimeter of site being more commonly used. Maintenance dosages over a prolonged period of time, e.g., daily administration for weeks to months, may be adjusted as necessary.

For veterinary uses higher levels may be administered as necessary. Determining actual amounts of the peptide-metal complexes necessary to treat a particular condition as described herein will be through standard empirical methods well known in the veterinary art. A representative lotion formulation for application to the skin comprises, in approximate amounts (expressed as final concentrations, w/v %): water, 62.9; cetyl alcohol, 5.0; stearic acid, 5.0; ARLACEL 165, 7.0; LEXOL EHP, 4.0; squalene, 5.0; copper chloride-$2H_2O$, 0.40; soybean peptone, 6.0; mineral oil, 3.0; allantoin, 0.5; GERMABEN-II-E, 1.0; herbal fragrance, 0.1; aloe vera powder, 0.1; vitamin A-D, 0.01; vitamin E, 0.01.

The peptide-metal complexes of the invention may be administered in relatively large amounts without serious side effects, although indiscriminate use may produce discoloration of the skin.

The peptide-metal complexes of the invention may be administered in methods to remove or diminish scars, such as scars of surgical, acne, or burn origin. The peptide-metal complexes can also be used to diminish or remove calluses, benign skin moles, multiple facial keratosis, vitiligo marks, thickened sun spots, and the like, by facilitating and speeding the process of skin remodeling. The methods comprise administering to the scar or site of skin blemish or imperfection a therapeutically effective amount of a composition which comprises the peptide-metal complex described herein in an amount and for a length of time sufficient to enhance the skin remodeling process and remove the skin imperfection. For these treatments, the skin layer is intact, as opposed to an open wound or sore, or other condition in which the skin is broken.

The methods can be used to reduce surgical scar formation by administering the peptide-metal complexes immediately after surgery. The methods comprise administering to the incision area a prophylactically effective amount of a composition comprising a peptide-metal complex.

In some treatments, a synergistic effect may be attained by combining the peptide-metal complexes with exfoliating agents such as glycolic acid or chemicals such as retinal or retinoic acid. These combinations often yield a clinical efficacy greater than that realized with any single factor.

The following examples are offered by way of illustration, not by way of limitation.

Example I

Preparation of Active Peptone-Metal Complexes

This Example describes methods used in the preparation of the peptone-metal complexes having biological activities described further below. Soybean peptone was obtained from Sigma Chemical Company, St. Louis, Mo. (type IV, number P 0521), as was cupric chloride hydrate (no. C 6641), tin (II) chloride, 99% pure; and tin (IV) chloride, 99% pure were obtained from Aldrich Chemical Company, Milwaukee, Wis.

Soybean peptones (enzymatic digests of soybean protein) were dissolved in warm water (40° C.) at a concentration of 20% (weight/volume), then mixed with an aqueous solution of a metal salt (copper(II) chloride, tin(II) chloride, tin(IV) chloride, or zinc(II) chloride) at a salt concentration of 20% (w/v). The pH of each soybean peptide-metal complex mixture is adjusted with sodium hydroxide to a pH value between 6.0 and 7.0. The resulting precipitate containing the peptide-metal complexes is removed by centrifugation at 10,000 G for 20 minutes, then processed as a wet paste into further products, e.g., the sticky paste can be applied directly to the skin or more usually is formulated to a desired final concentration into creams, lotions, sprays, etc.

Other types of enzymatic protein digests such as those of casein, collagen, elastin, meat products, silk protein and the like, and other metal salts of the metals, such as sulfate, acetate, phosphate and so forth will work similarly.

Example II

Preparation of Active Peptide-Metal Complexes

The synthetic peptides Gly-His-Lys, Gly-His-Lys-His (SEQ ID NO: 1), Gly-Gly-His, His-Gly-Gly, Gly-Gly, Gly-Gly-Gly, Ala-Gly-His, Phe-Phe, and Gly-Cys-Gly were either purchased from commercial sources or prepared by solid phase peptide synthesis by standard methods (Pickart and Thaler, Nature New Biol 243: 85-7 (1973)) although virtually any small peptide appears to function similarly. Synthetic peptides are commercially available from sources such as Sigma Chemical Company, St. Louis, Mo. and custom manufacturers.

Peptides were dissolved in warm water (40° C.) at a concentration of 20% (weight/volume), then mixed with an aqueous solution of a metal salt (copper(II) chloride, tin(II) chloride, tin(IV) chloride, or zinc(II) chloride) at a salt concentration of 20% (w/v).

Example III

Reduction in Scar Formation after Surgical Incisions Using Peptone-Copper, -Tin(II), -(Tin (IV), and -Zinc Complexes This Example describes the use of a pastes prepared with the complexes of peptone with copper (II), tin (II), tin (IV), and zinc (II) to reduce scarring after surgery in animals.

Surgical incisions (1.25 cm) were made on the backs of anesthetized, 35 gram, Swiss-Webster mice. Immediately after surgery and 24 hours later, the wounds were covered with a thin film of the paste containing the active peptone-copper complex in Example I above. Control wounds were untreated. As seen in Table I, wounds treated with the peptide-copper complexes and peptide-tin complexes had much less post-surgical scar formation than control wounds.

For comparison, the amount of scar formation was rated from 0 (little or no scarring) to 4 (heavy scarring).

TABLE 1

| Effect of peptone-copper complex on scar formation | |
|---|---|
| Test group of 20 mice | Scar Formation score after 5 days |
| Control | 3.2 + 0.4 |
| Peptone-Copper(II) complex | 0.2 + 0.1 |
| Peptone-Tin(II) complex | 0.1 + 0.1 |
| Peptone-Tin(IV) complex | 0.3 + 0.1 |
| Peptone-Zinc(II) Complex | 2.6 + 0.7 |

The results, shown in Table 1, indicate that wounds treated with the peptone-copper and tin complexes had much less post-surgical scar formation than control wounds, and peptone-zinc complexes were less active.

Example IV

Reduction in Scar Formation after Surgical Incisions with Synthetic Peptide Complexes of Copper(II) and Tin(II)

This Example describes the use of a synthetic peptides complexed with cupric chloride or Tin(II) chloride to reduce post-surgical scarring.

Peptide-copper complexes were dissolved in 0.85% saline at a concentration of 1 milligram per milliliter. Copper complexes of cysteic acid, cysteine sulfinic acid, and homocysteic acid were also tested.

Surgical incisions (1.25 cm) were made on the backs of anesthetized, 35 gram, Swiss-Webster mice. Immediately after surgery and 24 hours later, the 0.02 ml of the peptide complexes were injected at four sites on each side of the incision line. Control wounds were untreated. As seen in Table 2, wounds treated with the peptide-copper and tin complexes had much less post-surgical scar formation than control wounds. Copper complexes of cysteic acid, cysteine sulfinic acid, and homocysteic acid were much less active.

For comparison, the amount of scar formation was rated from 0 (little or no scarring) to 4 (heavy scarring).

TABLE 2

Effect of synthetic peptide-copper complexes and copper tin complexes on scar formation

| Test group (10 mice each) | Scar Formation score (5 days) |
|---|---|
| Control | 3.6 + 0.4 |
| Gly-His-Lys-Copper(II) | 0.2 + 0.1 |
| Gly-His-Lys-Tin(II) | 0.4 + 0.1 |
| Gly-His-Lys-His-Copper(II) | 0.4 + 0.2 |
| Gly-His-Lys-His-Tin(II) (SEQ ID NO: 1) | 0.4 + 0.2 |
| Gly-Gly-His-Copper(II) | 0.3 + 0.2 |
| His-Gly-Gly-Copper(II) | 0.5 + 0.2 |
| His-Gly-Gly-Tin(II) | 0.4 + 0.2 |
| Gly-Gly-Gly-Copper(II) | 0.5 + 0.3 |
| Ala-Gly-His-Copper(II) | 0.3 + 0.1 |
| Ala-Gly-His-Tin(II) | 0.3 + 0.1 |
| Phe-Phe-Copper(II) | 0.5 + 0.3 |
| Gly-Cys-Gly-Copper(II) | 1.4 + 0.3 |
| Cysteic acid-Copper(II) | 2.4 + 0.6 |
| Cysteine sulfinic acid-Copper(II) | 2.9 + 0.5 |
| Homocysteic acid-Copper(II) | 2.6 + 0.6 |

Example V

Removal of Skin Tags with Peptide-Copper Complex in a Cream Base

This Example demonstrates that the removal of skin tags (fibroepithelial papilloma) treated with the peptide-copper complex in a topical cream ointment showed reduced scars. The copper soy peptone complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A woman 52 years old had a chronic problem with skin tags. Many of these had been removed surgically but this always left scars. The cream was applied daily along with a 14% glycolic acid cream and most skin tags fell off within three weeks of daily treatment with the two creams. More resistant skin tags turned red and became about twice their normal size. Then in one or two days after turning red, they shriveled up and fell off. At the place the skin tags had been the skin was normal and scar free.

Example VI

Removal of Acne Scars with Peptide-Copper Complex in a Cream Base

This Example demonstrates that the removal of an acne scars treated with the peptide-copper complex in a topical cream ointment showed reduced scars. The copper soy peptide complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A woman 34 years old had old acne scars on her face. The cream was applied daily and the acne scars faded after three months of treatment.

Example VII

Removal of Foot Calluses with Peptide-Copper Complex in a Cream Base

This Example demonstrates that the removal of foot calluses with the peptone-copper complex in a topical cream ointment showed reduced scars. The copper soy peptone complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A man 60 years old had foot calluses that would split open and become sores. No other therapy had solved this problem. After two months of daily application with the cream, all of the calluses were healed and markedly reduced in size.

Example VIII

Removal of Benign Skin Mole with Peptide-Copper Complex in a Cream Base

This Example demonstrates the removal of a benign skin mole with the peptone-copper complex in a topical cream ointment. The copper soy peptide complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A man age 54 had a protruding benign mole-like growth surgically removed from his face 9 years previous. It returned within a year and became about ¼" thick and was growing. After using the cream for 6 weeks, the growth was removed. This person also found the cream removed age spots on his hands.

Example IX

Removal of Stretch Marks with Peptide-Copper Complex in a Cream Base

This Example demonstrates the removal of stretch marks with the peptone-copper complex in a topical cream ointment. The copper soy peptone complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A woman age 34 had stretch marks from two pregnancies. She applied the cream plus a 8% glycolic acid cream to the marks for three months and found they had disappeared.

Example X

Removal of Multiple Facial Keratosis with Peptide-Copper Complex in a Cream Base This Example demonstrates that the removal of facial keratosis with the peptone-copper complex in a topical cream ointment showed reduced scars. The copper soy peptone complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A woman age 32 had many raised age spots (keratosis) on her face. Her dermatologists said there were too many for effective removal with liquid nitrogen and other treatments had not worked. The cream was applied for 4 months and she reported that 75% of the keratosis had disappeared and the remainder were much smaller and shrinking.

Example XI

Removal of Keloid Scars with Peptide-Copper Complex in a Cream Base

This Example demonstrates that the removal of keloid scars with the peptide-copper complex in a topical cream ointment. The copper soy peptide complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A man age 21 had raised many keloid scars on his back from severe acne. They average 2 centimeters in diameter and were raised. Previous therapies had not reduced the scars and dermatologists felt any therapy might increase the scarring. After two weeks of treatment with the copper-peptide complex the scars started to flatten and get smaller. After 2 months of this treatment there was nearly total clearing of all keloid scars.

Example XII

Removal of Burn Scars with Peptide-Copper Complex in a Cream Base

This Example demonstrates removal of burn scars with the peptone-copper complex in a topical cream ointment. The copper soy peptide complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A man age 27 had two surface burn scars on his right forearm, each about 1.5 inches long, and about ½ inch wide, oval shaped and dark brown in color. Both scars were over 2 years in age. The first scar was removed after one week of copper-peptide complex cream use, the second after five weeks.

Example XIII

Removal of Thickened Sun Spots with Peptide-Copper Complex in a Cream Base

This Example demonstrates that thickened sunspots can be removed with the peptide-copper complex in a topical cream ointment. The copper soy peptide complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A woman age 31 with very fair skin had numerous thickened sunspots on her face and body. Some of these lesions were ten years old. Removal of the spots by a dermatologist would almost always result in regrowth. She applied the cream plus a 8% glycolic acid cream to the lesions daily. In three weeks most of the lesions were gone leaving only a reddish skin area. Further use of the creams eliminated this reddish area in about a month. Later she reported that the lesions seemed to be permanently removed.

Example XIV

Removal of Scars from Sjogren's Syndrome with Peptide-Copper Complex in a Cream Base This Example demonstrates the removal of scars from Sjogren's syndrome with the peptide-copper complex in a topical cream ointment. The copper soy peptide complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A woman age 49 had Sjogren's syndrome which produced very dry skin that cracked and became inflamed and left scars on her fingers and face. She had used steroid ointments but they left noticeable scars. After one month of using the copper-peptide cream her skin became less dry and the skin stopped cracking. After four months of treatment all of the scars were removed from her face and hands.

Example XV

Removal of Vitiligo Marks with Peptone-Copper Complex in a Cream Base

This Example demonstrates the reduction of vitiligo marks (markedly lighter patches on skin) with the peptone-copper complex in a topical cream ointment. The copper soy peptone complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A man age 61 reported that he had vitiligo marks on his hands for 35 years. After using the copper-peptide cream for one year, he found the vitiligo marks to be nearly invisible. Normal colored skin had replaced almost all of the vitiligo patches.

Example XVI

Removal of Surgical Scars with Peptide-Copper Complex in a Cream Base

This Example demonstrates the reduction of surgical scars with the peptide-copper complex in a topical cream ointment. The copper soy peptone complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A man age 45 had two-year-old surgical scars on his arm. After using the copper peptide cream plus a 14% glycolic acid cream for three months he reported that the scars had disappeared.

Example XVII

Prevention of Scars after Hand Surgery with Peptide-Copper Complex in a Cream Base This Example demonstrates the prevention of scar formation after surgery with the peptide-copper complex in a topical cream ointment. The copper soy peptone complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol.

A man age 43 had extensive reconstructive surgery on his hand. Immediately after surgery, he applied the cream and continued using the cream for one month. He reported that there was no scarring and the hand looked completely normal.

All publications and patents mentioned in this specification are indicative of the level of skill of those skilled in the art to which this invention pertains. All publications and patents are herein incorporated by reference to the same extent as if each individual publication or patent was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for stimulating remodeling of blemished skin in a mammal, comprising administering to the intact blemished skin of said mammal a composition that comprises a peptone digest complexed with an ionic metal in an amount effective to remodel the skin and diminish or remove the skin blemish, wherein the peptone digest is a hydrolysate of casein, collagen, elastin, meat protein, silk protein, or soybean protein.

2. The method according to claim 1, wherein the skin blemish is a scar.

3. The method according to claim 2, wherein the scar is selected from the group consisting of an acne scar, a keloid scar, and a Sjogren's syndrome scar.

4. The method according to claim 1, wherein the skin blemish is selected from the group consisting of skin tags, calluses, benign skin moles, stretch marks, facial keratosis, thickened sunspots of the skin, and vitiligo spots.

5. The method of claim 1, wherein the ionic metal is selected from the group consisting of copper(II), tin(II), tin (IV), and zinc(II), and therapeutically acceptable salts and complexes thereof.

6. The method of claim 1, wherein the ionic metal is copper (II).

7. The method according to claim 1, wherein the peptone digest is an enzymatic hydrolysis of casein, collagen, elastin, meat protein, silk protein, or soybean protein.

8. The method according to claim 1, wherein the peptone digest is an acid hydrolysis of casein, collagen, elastin, meat protein, silk protein, or soybean protein.

9. The method according to claim 1, wherein the peptone digest is a basic hydrolysis of casein, collagen, elastin, meat protein, silk protein, or soybean protein.

10. The method according to claim 1, wherein the peptone digest is a bacterial hydrolysis of casein, collagen, elastin, meat protein, silk protein, or soybean protein.

11. The method according to claim 1, wherein the composition is administered topically or by injection into the skin.

12. The method according to claim 1, wherein the peptone digest complexed with an ionic metal is combined with a carrier to form a cream or lotion.

13. The method according to claim 1, wherein the concentration of the peptone digest complexed with an ionic metal in the composition is 1% to 25%.

* * * * *